United States Patent
Hayakawa et al.

(10) Patent No.: US 7,268,150 B2
(45) Date of Patent: Sep. 11, 2007

(54) 2-CYANO-4-FLUOROPYRROLIDINE DERIVATIVE OR ITS SALT

(75) Inventors: Masahiko Hayakawa, Tsukuba (JP); Kenji Negoro, Tsukuba (JP); Satoshi Miyamoto, Tsukuba (JP); Takayuki Suzuki, Tsukuba (JP); Tatsuya Maruyama, Tsukuba (JP); Ryosuke Nakano, Tsukuba (JP)

(73) Assignee: Yamanouchi Pharmaceutical Co., Ltd., Tokyo (JP)

( * ) Notice: Subject to any disclaimer, the term of this patent is extended or adjusted under 35 U.S.C. 154(b) by 545 days.

(21) Appl. No.: 10/492,347

(22) PCT Filed: Jul. 18, 2003

(86) PCT No.: PCT/JP03/09179

§ 371 (c)(1),
(2), (4) Date: Apr. 13, 2004

(87) PCT Pub. No.: WO2004/009544

PCT Pub. Date: Jan. 29, 2004

(65) Prior Publication Data

US 2005/0176771 A1    Aug. 11, 2005

(30) Foreign Application Priority Data

Jul. 23, 2002  (JP)  ............................. 2002-213654
Sep. 10, 2002  (JP)  ............................. 2002-264450

(51) Int. Cl.
*A61K 31/445* (2006.01)
*C07D 207/16* (2006.01)

(52) U.S. Cl. ..................................... 514/326; 546/208
(58) Field of Classification Search ................ 514/304, 514/321, 326, 422; 546/124, 197, 208; 548/518
See application file for complete search history.

(56) References Cited

U.S. PATENT DOCUMENTS

| 6,166,063 A | 12/2000 | Villhauer ..................... 514/423 |
| 2004/0063935 A1 | 4/2004 | Yasuda et al. |
| 2004/0072892 A1 | 4/2004 | Fukushima et al. |
| 2004/0242636 A1* | 12/2004 | Haffner et al. ............... 514/326 |
| 2005/0130981 A1* | 6/2005 | Aranyl et al. ........... 514/252.03 |

FOREIGN PATENT DOCUMENTS

| WO | WO98/19998 | 5/1998 |
| WO | WO 01/55105 A1 | 8/2001 |
| WO | WO 01/96295 | 12/2001 |
| WO | WO 03/000250 A1 | 1/2003 |
| WO | WO 03/000253 A2 | 1/2003 |

* cited by examiner

*Primary Examiner*—Celia Chang
(74) *Attorney, Agent, or Firm*—Finnegan, Henderson, Farabow, Garrett & Dunner, LLP

(57) ABSTRACT

Provided is a compound having excellent dipeptidyl peptidase IV-inhibiting activity, and a remedy based on the activity for insulin-dependent diabetes (type 1 diabetes), especially for non insulin-dependent diabetes (type 2 diabetes), insulin-resistant disorders, and obesity.

5 Claims, No Drawings

2-CYANO-4-FLUOROPYRROLIDINE DERIVATIVE OR ITS SALT

This application is the National Stage of International Application No. PCT/JP2003/009179, filed Jul. 18, 2003.

TECHNICAL FIELD

The present invention relates to a novel 2-cyano-4-fluoropyrrolidine derivative or a salt thereof useful as a drug, especially for dipeptidyl peptidase IV (hereinafter referred to as "DPP-IV") inhibitor and to a pharmaceutical composition comprising the compound as an active ingredient.

BACKGROUND ART

Dipetidyl peptidase-IV (DPP-IV) is a serine protease that recognizes and cuts a sequence with proline, hydroxyproline or alanine at the 2nd position from the N-terminal thereof (H-Xaa-Pro, H-Xaa-Hyp or H-Xaa-Ala, in which Xaa indicates an amino acid). It is known that DPP-IV is broadly distributed in humans, not only in tissues of the kidneys, liver, and salivary glands, but also in body fluids such as serum, urine, and saliva. Though its physiological role has not been completely clarified as yet, DPP-IV may participate in regulating biological functions as it cuts various physiologically-active peptides(non-patent reference 1). In particular, it is now specifically noticed that DPP-IV may control the activity of a hormone, incretin that participates in inhibiting blood glucose increase.

Incretin is a hormone that is secreted from the intestines after nutrient ingestion in humans, and it acts on pancreatic β-cells to enhance insulin secretion, thereby regulating the blood glucose level. It is known that the incretin activity is attenuated in type 2 diabetics (non-patent reference 2), and it is considered that the activity attenuation will be one reason for the expression of diabetes. Accordingly, it is expected that the postprandial hyperglycemia of diabetics could be ameliorated.

At present, glucagon-like peptide (hereinafter referred to as "GLP-1") is known as a compound that exhibits a most effective incretin activity in humans. GLP-1 is, after secreted in blood, immediately inactivated, and it is known that the inactivation is essentially owing to the action of DPP-IV that cleaves it (non-patent reference 3). Further, the inactive GLP-1 cleaved by DPP-IV binds to a GLP-1 receptor and prevents active GLP-1 from binding to the receptor. Accordingly, it is believed that the incretin action of GLP-1 is thereby attenuated (non-patent reference 4).

For these reasons, it is believed that a DPP-IV inhibitor may prevent the inactivation of GLP-1, therefore enhancing the incretin action of active GLP-1, and, as a result, it may prevent the postprandial hyperglycemia of diabetics. In addition, since incretin enhances the glucose-dependent insulin secretion in humans, it is expected that the DPP-IV inhibitor may be a safe remedy without side effect such as hypoglycemia which is often seen in use of existing insulin-secretion remedies.

On the other hand, some 2-cyanopyrrolidine derivatives are known, having a DPP-IV inhibiting activity (patent references 1 to 7).

Of those, International Publication WO02/30890 pamphlet (patent reference 5) specifically discloses compounds of a general formula (A), saying that the compounds will be effective for prevention and remedy of diabetes and for prevention and remedy of other diseases that are induced or exacerbated by impaired glucose tolerance, hyperinsulinemia and diabetic complications.

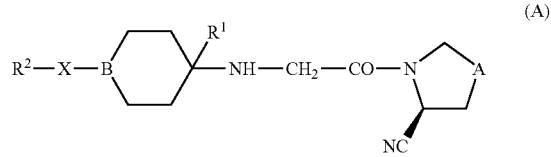

(In the formula, the symbols are as defined in the patent document.)

On the other hand, International Publication WO02/38541 pamphlet (patent reference 6) discloses compounds of a general formula (B), saying that the compounds significantly inhibit the blood glucose level increase in an oral glucose tolerance test with Zucker Fatty rats.

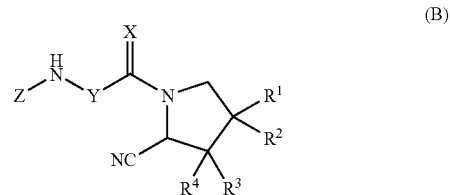

(In the formula, the symbols are as defined in the patent document.)

International Publication WO03/002553 pamphlet (patent reference 7) discloses compounds of general formulae (C), (D), (E), (F), (G) and (H), saying that the compounds are useful for treating disorders such as diabetes, obesity.

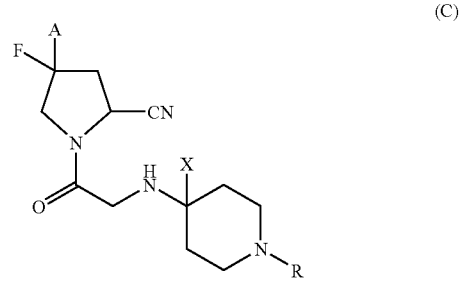

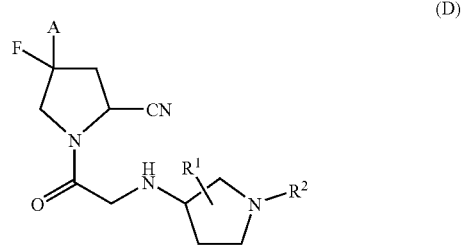

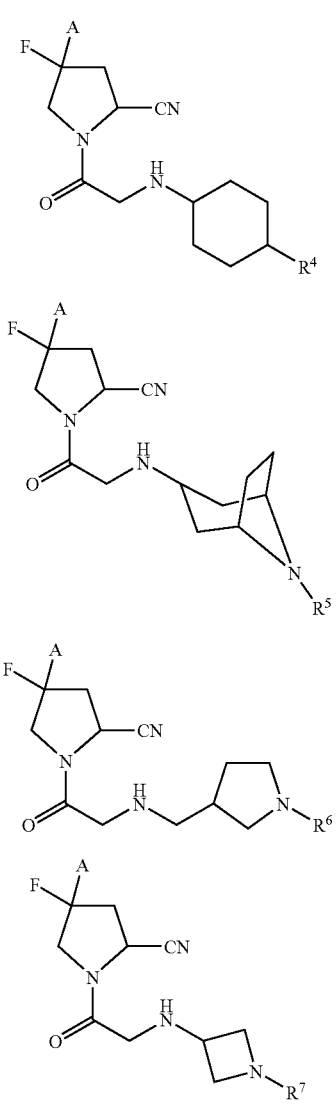

(In the formula, the symbols are as defined in the patent document.)

Given that situation, it is greatly desired to develop drugs that have more excellent DPP-IV inhibiting activity.

Non-patent reference 1: Mentlein R., Regulatory Peptide, 1999, Vol. 85, pp. 9-24.

Non-patent reference 2; Nauck M. A., Diabetologia, 1986, Vol. 29, pp. 46-52.

Non-patent reference 3; Drucker D. J., Diabetes, 1998, Vol. 47, pp. 159-169

Non-patent reference 4: Knudsen L. B., European Journal of Pharmacology, 1996, Vol. 318, pp. 429-435.

Patent reference 1: International Publication WO98/19998 pamphlet.

Patent reference 2: International Publication WO01/96295 pamphlet.

Patent reference 3: International Publication WO00/34241 pamphlet.

Patent reference 4: International Publication WO01/55105 pamphlet.

Patent reference 5: International Publication WO02/30890 pamphlet.

Patent reference 6: International Publication WO02/38541 pamphlet.

Patent reference 7: International Publication WO03/002553 pamphlet.

DISCLOSURE OF THE INVENTION

The present inventors made extensive and intensive investigations with respect to compounds having a DPP-IV inhibiting activity, which are expected to be effective for insulin-dependent diabetes (type 1 diabetes), non insulin-dependent diabetes (type 2 diabetes), insulin-resistant disorders and obesity. As a result, it has been found that a novel 2-cyano-4-fluoropyrrolidine derivative or a salt thereof of the invention has an excellent DPP-IV inhibiting activity, leading to accomplishment of the invention.

Accordingly, the invention provides a 2-cyano-4-fluoropyrrolidine derivative of the following general formula (I) or a pharmaceutically acceptable salt thereof that is useful as a DPP-IV inhibitor.

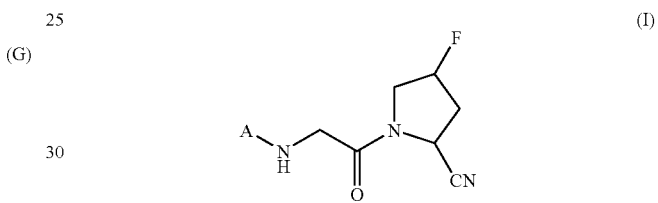

wherein A represents piperidin-4-yl, oxetan-3-yl, pyrrolidin-3-yl, tetrahydro-2H-pyran-4-yl, pyrazolidin-4-yl, 1,3-dioxan-5-yl, 8-azabicyclo[3.2.1]oct-3-yl or tetrahydro-2H-thiopyran-4-yl, each of which may be substituted, but excluding piperidin-4-yl which is substituted with a group selected from the group consisting of propane-2-sulfonyl, 2,4,6-trimethylbenzenesulfonyl, phenylmethanesulfonyl, 2-naphthalen-1-ylethanesulfonyl, 7,7-dimethyl-6-oxonorbornan-1-ylmethanesulfonyl, 4-fluorophenyl, 3,5-difluorophenyl, 4-nitrophenyl, 4-trifluoromethylphenyl, 4-cyanophenyl, 4-cyano-3-fluorophenyl, 4-cyano-3,5-difluorophenyl, 3-cyano-5-fluorophenyl, benzoxazol-2-yl and benzyl; pyrrolidin-3-yl which is substituted with a group selected from the group consisting of propane-2-sulfonyl, 3-cyanopyridin-6-yl, 4-trifluoromethylphenyl, 4-fluorophenyl and 4-fluorobenzyl; and 8-azabicyclo[3.2.1]oct-3-yl which is substituted with ethoxycarbonyl.

In the formula (I), A is preferably piperidin-4-yl or 8-azabicyclo[3.2.1]oct-3-yl, each of which may be substituted, more preferably a group of a general formula (II):

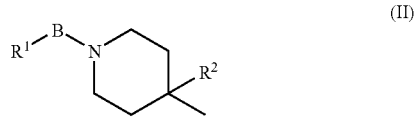

wherein B represents carbonyl, sulfonyl or single bond;
$R^1$ represents lower alkyl, aryl or aromatic hetero ring, each of which may be substituted;
$R^2$ represents lower alkyl which is optionally substituted with a group selected from the group consisting of —OH and —O-lower alkyl, or represents —H.

In formula (II), B is preferably carbonyl or sulfonyl.

In formula (II), $R^1$ is preferably lower alkyl which is optionally substituted, more preferably lower alkyl which is optionally substituted with a group selected from the group consisting of —OH and fluoro, even more preferably methyl or ethyl, each of which is optionally substituted with a group selected from the group consisting of —OH and fluoro, most preferably methyl or ethyl, each of which is optionally substituted with —OH.

In formula (II), $R^2$ is preferably lower alkyl which is optionally substituted with —OH, more preferably methyl or ethyl, each of which is optionally substituted with —OH, even more preferably methyl, ethyl or hydroxymethyl, most preferably methyl.

The chemical structure of the 2-cyano-4-fluoropyrrolidine derivatives of the invention is characterized in that an optionally substituted non-aromatic hetero ring bonds to the 1-position of a 2-cyano-4-fluoropyrrolidine skeleton via aminomethylenecarbonyl, and the pharmaceutical characteristic thereof is that the derivatives have a DPP-IV inhibiting activity.

Of the compounds of formula (I), preferred are those where A is piperidin-4-yl or 8-azabicyclo[3.2.1]oct-3-yl, each of which is optionally substituted; more preferred are those where A is a group of formula (II); even more preferred are those where A is a group of formula (II), B is carbonyl or sulfonyl, $R^1$ is optionally substituted lower alkyl, $R^2$ is methyl, ethyl or hydroxymethyl; and most preferred are those where A is a group of formula (II), B is carbonyl or sulfonyl, $R^1$ is methyl or ethyl, each of which is optionally substituted with a group selected from the group consisting of —OH and fluoro, $R^2$ is methyl.

Of those compounds, especially preferred are the following:

4-fluoro-1-({[1-(methanesulfonyl)piperidin-4-yl]amino}acetyl)pyrrolidine-2-carbonitrile, 4-fluoro-1-({[4-methyl-1-(methanesulfonyl)piperidin-4-yl]amino}acetyl)pyrrolidine-2-carbonitrile, 4-fluoro-1-{[(1-glycoloylpiperidin-4-yl)amino]acetyl}pyrrolidine-2-carbonitrile, 4-fluoro-1-{[(1-glycoloyl-4-methylpiperidin-4-yl)amino]acetyl}pyrrolidine-2-carbonitrile, 4-fluoro-1-{[(1-fluoroacetyl-4-methylpiperidin-4-yl)]amino]acetyl}pyrrolidine-2-carbonitrile, 4-fluoro-1-{[(1-formylpiperidin-4-yl)amino]acetyl}pyrrolidine-2-carbonitrile, 4-fluoro-1-{[(1-formyl-4-methylpiperidin-4-yl)amino]acetyl}pyrrolidine-2-carbonitrile, or 4-fluoro-1-({[1-(morpholin-4-ylcarbonyl)piperidin-4-yl]amino}acetyl)pyrrolidine-2-carbonitrile, or a pharmaceutically acceptable salt thereof; more preferred are the following:

4-fluoro-1-({[4-methyl-1-(methanesulfonyl)piperidin-4-yl]amino}acetyl)pyrrolidine-2-carbonitrile, or 4-fluoro-1-{[(1-glycoloyl-4-methylpiperidin-4-yl)amino]acetyl}pyrrolidine-2-carbonitrile, or a pharmaceutically acceptable salt thereof.

In another preferred embodiment of the compounds of formula (I), A is a group of formula (II) and B is carbonyl.

The invention further provides a pharmaceutical composition comprising, as an active ingredient, the compound mentioned above, especially a pharmaceutical composition comprising, as an active ingredient, the compound mentioned above for remedies and/or preventives for insulin-dependent diabetes (type 1 diabetes), non insulin-dependent diabetes (type 2 diabetes), insulin-resistant disorders or obesity; and a pharmaceutical composition comprising, as an active ingredient, the compound mentioned above for dipeptidyl peptidase IV inhibitor.

The compounds of the invention will be further described hereinunder.

In this description, "lower alkyl" means a $C_{1-6}$ linear or branched alkyl, for example, concretely including methyl, ethyl, propyl, isopropyl, butyl, tert-butyl, pentyl, neopentyl and hexyl, etc. Preferably, it is methyl, ethyl, propyl or isopropyl, more preferably methyl or ethyl.

"Aryl" means a $C_{6-14}$ monocyclic to tricyclic, aromatic monovalent group consisting of carbon atoms, for example, concretely including phenyl and naphthyl, etc. Preferably, it is phenyl.

"Aromatic hetero ring" means a monocyclic to tricyclic aromatic monovalent group having at least one hetero atom selected from the group consisting of nitrogen, oxygen and sulfur atoms, for example, concretely including furanyl, thienyl, pyrrolyl, pyridyl, oxazolyl, thiazolyl, isothiazolyl, imidazolyl, pyrazolyl, tetrazolyl, pyrazinyl, pyrimidinyl, pyridazinyl, triazinyl, isoxazolyl, triazolyl, benzofuranyl, benzothienyl, benzothiadiazolyl, benzothiazolyl, benzoxazolyl, benzimidazolyl, benzotriazolyl, indolyl, isoindolyl, quinazolyl, quinolyl, isoquinolyl, quinoxayl, imidazopyridinyl and imidazopyrimidinyl, etc. Preferably, it is pyridyl.

The acceptable substituent for the optionally-substituted "piperidin-4-yl, oxetan-3-yl, pyrrolidin-3-yl, tetrahydro-2H-pyran-4-yl, pyrazolidin-4-yl, 1,3-dioxan-5-yl, 8-azabicyclo[3.2.1]oct-3-yl or tetrahydro-2H-thiopyran-4-yl" for A may be any and every one generally usable for these groups, and the group A may have one or more, preferably from 1 to 4 substituents. Including the carbon atom of A that directly bonds to the group NH in formula (I), the carbon atom or the nitrogen atom of the ring may be substituted. In addition, the sulfur atom of the ring may be oxidized.

The substituent to bond to the carbon atom includes a substituent group X, —OH, —O—X, halogen, —CO—X, —COO—X, —SO$_2$—X and —CONRR'. Preferably, it is lower alkyl or aryl, each of which is optionally substituted with one or more group selected from the group consisting of —OH, —O-lower alkyl, —O-aryl, halogen, cyano and nitro, more preferably lower alkyl optionally substituted with a substituent selected from —OH and fluorine.

R and R' may be the same or different, representing lower alkyl optionally substituted with —OH, or —H (the same shall apply hereinunder). "Substituent group X" is meant to include lower alkyl, lower alkenyl, lower alkynyl, cycloalkyl, cycloalkenyl, aryl, non-aromatic hetero ring and aromatic hetero ring, each of which is optionally substituted with one or more group selected from the group consisting of —OH, —O-lower alkyl, —O-aryl, halogen, cyano and nitro (the same shall apply hereinunder).

On the other hand, the substituent to bond to the nitrogen atom includes a substituent group X, —CO—X, —COO—X, —SO$_2$—X, and —CONRR'. Preferably, it is lower alkyl, cycloalkyl, aryl or aromatic hetero ring, each of which is optionally substituted with one or more substituent selected from the group consisting of —OH, —O-lower alkyl, —O-aryl, halogen, cyano and nitro; or —SO$_2$-lower alkyl (optionally substituted with one or more substituent selected from the group consisting of —OH, —O-lower alkyl, —O-aryl, halogen, cyano and nitro); or —SO$_2$-aryl (optionally substituted with one or more substituent selected from the group consisting of —OH, —O-lower alkyl, —O-aryl, halogen, cyano and nitro).

"Lower alkenyl" means a $C_{2-6}$ alkenyl, for example, concretely including vinyl, allyl, 1-propenyl, 1-butenyl, 2-butenyl and 3-butenyl.

"Lower alkynyl" means a $C_{2-6}$ alkynyl, for example, concretely including ethynyl, 1-propynyl, 2-propynyl, 1-butynyl, 2-butynyl and 3-butynyl.

"Cycloalkyl" means a $C_{3-14}$ monovalent residue of a carbon ring, and this may be bridged fused. Concretely, for example, it includes cyclopropyl, cyclopentyl, cyclohexyl, cyclooctyl, adamantyl, bornyl, norbornyl, bicyclo[2.2.1]heptyl, bicyclo[3.1.1]heptyl, bicyclo[2.2.2]octyl, bicyclo[3.2.1]octyl and bicyclo[3.3.1]nonyl.

"Cycloalkenyl" means a $C_{3-14}$ carbon ring residue that corresponds to the "cycloalkyl" but is partially unsaturated, for example, concretely including cyclopentenyl, cyclohexenyl and norbornenyl.

"Halogen" includes fluoro, chloro, bromo and iodo. Preferably, it is fluoro, chloro or bromo, more preferably fluoro.

The compounds of the invention include mixtures of various stereoisomers such as tautomeric isomers and optical isomers, and those isolated from them.

The compounds of the invention may form acid-addition salts. Depending on the type of the substituent therein, they may form salts with bases. Concretely, the salts include acid-addition salts with mineral acids such as hydrochloric acid, hydrobromic acid, hydroiodic acid, sulfuric acid, nitric acid, phosphoric acid, or with organic acids such as formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, p-toluenesulfonic acid; salts with acidic amino acids such as aspartic acid, glutamic acid, or with inorganic bases such as sodium, potassium, magnesium, calcium, aluminium, or with organic bases such as methylamine, ethylamine, ethanolamine; or with basic amino acids such as lysine, ornithine; and ammonium salts.

The compounds of the invention further include hydrates, various pharmaceutically acceptable solvates, and polymorphic crystals. Naturally, the invention should not be limited to the compounds described in Examples given hereinunder, and include all derivatives of formula (I) and their pharmaceutically acceptable salts.

Incidentally, the compound of the invention includes all of so-called prodrugs, i.e., compounds that will be metabolized and converted into the compound of the foregoing general formula (I) or its salt within humans. As the group to form the prodrug are enumerated those groups described in *Prog. Med.*, 5, 2157-2161 (1985) and *Iyakuhin No Kaihatsu* (Development of Drugs), Vol. 7, "Molecular Design", 163-198 (1990), by Hirokawa Publishing Co.

(Production Method)

The compound of the invention and its pharmaceutically acceptable salt can be produced through application of various known synthesis processes by utilizing the characteristic based on the basic skeleton thereof or kinds of the substituents. Incidentally, in some case, it is effective on the production technology that depending on the kind of a functional group, the functional group is replaced by a protective group, i.e., a group that can be readily converted into the functional group in a state of the starting material or intermediates. Thereafter, if desired, the protective group is removed, thereby enabling to obtain the desired compound. Examples of such a functional group include a hydroxyl group, a carboxyl group and an amino group. Examples of the protective group thereof include the protective groups as described in Greene and Wuts, *Protective Groups in Organic Synthesis* (*third edition*), and these may be properly used depending on the reaction conditions.

One typical production method is described below.

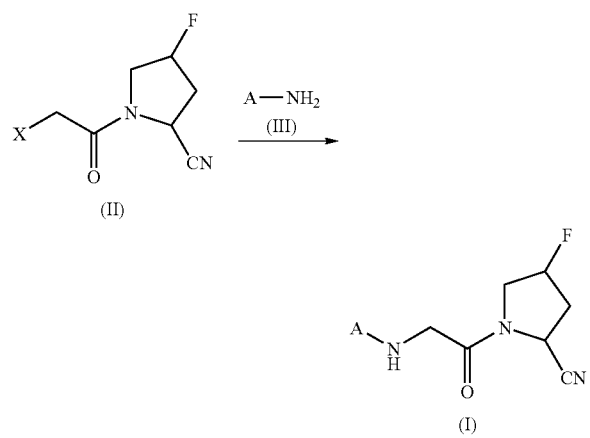

wherein A has the same meaning as above; and X represents a leaving group such as halogen or sulfonyloxy group.

The method comprises alkylation of a compound (II) with an amine (III) of a general formula, $A—NH_2$ to give the compound (I) of the invention. The reaction may be effected in the absence or presence of a solvent. The solvent may be any of aromatic hydrocarbons such as toluene, xylene; ketones such as methyl ethyl ketone, acetone; ethers such as dioxane, tetrahydrofuran, diglyme; alcohols such as methanol, ethanol, isopropanol; chloroform, methylene chloride, acetonitrile, dimethylformamide, dimethylsulfoxide, water; and their mixed solvents. Depending on the type of the reaction substrate and the reaction conditions, a suitable solvent may be selected for the reaction.

Adding a base to the reaction is preferred for smoothly effecting the reaction. Specific examples of the base are alkali carbonates such as sodium carbonate, potassium carbonate; alkali hydrogencarbonates such as sodium hydrogencarbonate, potassium hydrogencarbonate; and organic amines such as triethylamine, diisopropylethylamine, pyridine.

Some of the compounds of the invention may be produced from the compounds (I) obtained in the manner as above, by combining, in any desired manner, some known steps that may be generally employed by those skilled in the art, such as alkylation, acylation, oxidation, reduction, hydrolysis, etc.

Thus produced, the compounds of the invention may be isolated and purified as they are in the form of free compounds, or after salted into their salts in an ordinary manner. The isolation and purification may be effected in any ordinary chemical operation such as extraction, concentration, distillation, crystallization, filtration, recrystallization, various modes of chromatography, etc.

In case where the compounds of the invention have an asymmetric carbon, they include optical isomers. The optical isomers may be resolved in an ordinary manner, for example, through fractionating crystallization with recrystallization with a suitable salt or through column chromatography. The optical active compounds may be produced, starting from a suitable optical active compound.

INDUSTRIAL APPLICABILITY

The compounds of the invention have a DPP-IV inhibiting activity. Especially, they have an activity to inhibit the degradation of GLP-1, a hormone that acts on pancreatic β-cells to enhance insulin secretion to thereby regulate blood glucose.

Based on their effect, therefore, the compounds of the invention are useful for remedy and/or prevention of insulin-dependent diabetes (type 1 diabetes), especially non insulin-dependent diabetes (type 2 diabetes), insulin-resistant disorders, and obesity.

The excellent DPP-IV inhibiting activity of the compounds of the invention has been confirmed by the test methods mentioned below.

(1) Test for Determination of DPP-IV Inhibiting Activity:

The reaction was performed in a 96-well flat-bottom microtiter plate. A varying concentration of the test compound was added to an aqueous solution comprised of 25 mM Tris-HCl, 140 mM sodium chloride, 10 mM potassium chloride, 1% RIA-grade bovine serum albumin, and 0.01 mM Gly-Pro-AMC (Bachem). To this reaction solution (95 μL/well), added was 5 μL of plasma collected from healthy adult volunteers, and incubated at room temperature for 20 minutes. After the reaction, the fluorescence intensity (excitation 355 nm/emission 460 nm) of each well was measured (ARVO, Perkin Elmer). The data of 3 wells under the same conditions were averaged.

The inhibition in the test group, relative to the solvent-added group was calculated, and the $IC_{50}$ value thereof was obtained through logistic analysis. The result is given in Table 1.

TABLE 1

| test compound | $IC_{50}$/nM |
| --- | --- |
| Example 1 | 4.2 |
| Example 14 | 7.2 |
| Example 19 | 4.2 |
| Example 21 | 6.0 |
| Example 28 | 5.1 |
| Example 34 | 8.2 |
| Example 36 | 7.5 |
| Example 41 | 5.9 |

The above confirms the DPP-IV inhibiting activity of the compounds of the invention.

(2) Test for DPP-IV Inhibiting Activity Duration in Mice:

Male ICR mice (Nippon SLC) were grouped into a test group and a control group of 5 subjects each. A test compound (10 mg/kg) was dissolved in purified water, and orally administered. Purified water alone was orally administered to the mice of the control group. One half, 6, and 12 hours after the administration, the blood was collected from each mouse through the orbital venous plexus thereof. The collected blood was immediately centrifuged to isolate the plasma, and the DPP-IV activity of the plasma was measured.

The process of plasma DPP-IV activity determination was as follows: The reaction was performed in a 96-well plate. 5 μl of the collected plasma was added to an aqueous solution (95 μl/well) comprises 25 mM Tris-HCl, 140 mM sodium chloride, 10 mM potassium chloride, 1% bovine serum albumin, and 0.01 mM Gly-Pro-AMC (Bachem), and incubated at room temperature for 20 minutes. The fluorescence intensity (excitation 355 nm/emission 460 nm) of each well was measured (ARVO, Perkin Elmer).

The fluorescent intensity of the well, to which was added the plasma collected from the control group, was 100%. Based on it, the DPP-IV activity of the plasma collected from the test compound-administered mice was calculated, and the activity difference between the control group and the test group was obtained. This indicated the inhibition in the test group. The result is given in Table 2.

(3) Test for DPP-IV Inhibiting Activity Duration in Rats:

Male SD rats (Clea Japan) were grouped into a test group and a control group of 5 subjects each. A test compound (10 mg/kg) was dissolved in purified water, and orally administered. Purified water alone was orally administered to the rats of the control group. One half, 6, and 12 hours after the administration, the blood was collected from each rat through the tail vein thereof. The collected blood was immediately centrifuged to isolate the plasma, and the DPP-IV activity of the plasma was measured according to the same process as in the dipeptidyl peptidase-IV (DPP-IV) inhibiting activity duration test shown in (2).

The fluorescent intensity of the well, to which was added the plasma collected from the control group, was 100%. Based on it, the DPP-IV activity of the plasma collected from the test compound-administered rats was calculated, and the activity difference between the control group and the test group was obtained. This indicated the inhibition in the test group. The result is given in Table 3.

TABLE 2

Test for DPP-IV inhibiting activity duration in mice

| test compound | inhibition of plasma DPP-IV activity after 6 h/% | inhibition of plasma DPP-IV activity after 12 h/% |
| --- | --- | --- |
| Example 1 | 74 | 59 |
| Example 14 | 66 | 65 |
| Example 19 | 72 | 61 |
| Example 21 | 78 | 71 |
| Example 34 | 85 | 79 |
| Example 36 | 81 | 78 |
| Example 41 | 83 | 78 |

TABLE 3

Test for DPP-IV inhibiting activity duration in rats

| test compound | inhibition of plasma DPP-IV activity after 6 h/% | inhibition of plasma DPP-IV activity after 12 h/% |
| --- | --- | --- |
| Example 14 | 92 | 87 |
| Example 34 | 96 | 94 |
| Example 36 | 92 | 86 |
| Example 41 | 93 | 89 |
| Comparative Compound 1 | 65 | 38 |
| Comparative Compound 2 | 77 | 55 |
| Comparative Compound 3 | 80 | 45 |

In the Table 3, comparative compound 1 represents Example 4-9 described in patent reference 5, comparative compound 2 represents Example 4-17 described in patent reference 5, comparative compound 3 represents Example 33 described in patent reference 7; each patent reference is mentioned above. The structure of comparative compounds 1-3 will be shown below.

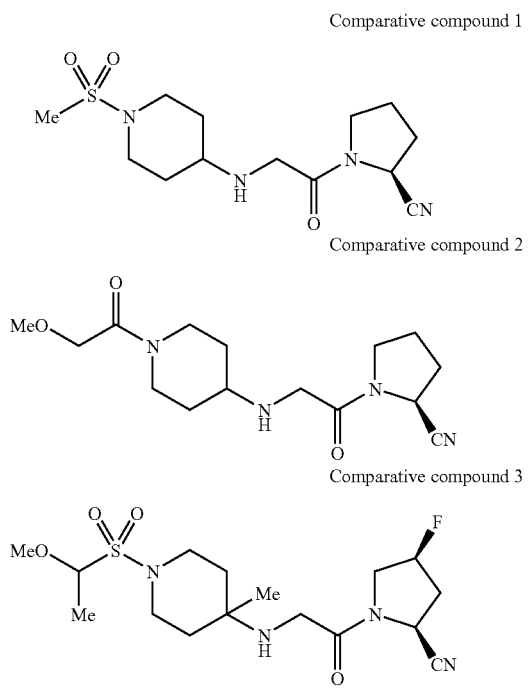

Comparative compound 1

Comparative compound 2

Comparative compound 3

Table 2 and Table 3 above show that the compounds of the present invention have good oral activities and their activities last even after 6 hours and 12 hours from their administration. These results confirm that the compounds of the present invention have better oral activities and duration in vivo in comparison with comparative compounds 1-3.

The pharmaceutical composition that contains, as an active ingredient, one or more of the compounds and their pharmaceutically acceptable salts of the invention may be prepared by the use of a carrier, a vehicle and other additives generally used in formulating pharmaceutical compositions. It may be orally or parenterally administered in any form of tablets, powders, fine granules, granules, capsules, pills, liquids, injections, suppositories, ointments or poultices.

The clinical dose of the compound of the invention may be suitably determined, depending on the condition, the body weight, the age and the sex of the patients to which it is administered, but is favorable, in general, from 0.1 to 500 mg/adult/day for oral administration, and from 0.01 to 100 mg/adult/day for parenteral administration. This may be administered to the patients all at a time, or may be divided into a few portions for administration in a few times. Since the dose varies depending on various conditions, it may be smaller than the range mentioned above.

As a solid composition for oral administration of the compounds of the invention, tablets, powders, granules, etc are used. The solid composition of those types comprises one or more active substances mixed with at least one inert diluent, such as lactose, mannitol, glucose, hydroxypropyl cellulose, microcrystalline cellulose, starch, polyvinyl pyrrolidone, magnesium metasilicate aluminate. In an ordinary manner, the composition may contain any other additives except the inert diluents noted above, for example, a lubricant such as magnesium stearate, a disintegrator such as calcium cellulose glycolate, a stabilizer such as lactose, and a solubilizer or dissolution promoter such as glutamic acid or aspartic acid. If desired, the tablets and pills may be coated with a film of sugar or gastric or enteric substances such as sucrose, gelatin, hydroxypropyl cellulose, hydroxypropylmethyl cellulose phthalate.

A liquid composition for oral administration includes, for example, pharmaceutically-acceptable emulsions, solutions, suspensions, syrups, elixirs and the like, which contain ordinary inactive diluents such as pure water or ethyl alcohol. In addition to the inert diluents, those compositions may further contain pharmaceutical aids such as solubilizers, dissolution aids, wetting promoters, suspension promoters, and also sweeteners, flavorings, aromas and preservatives.

Injection for parenteral administration includes, for example, germ-free, aqueous or non-aqueous solutions, suspensions and emulsions. The diluent for the aqueous solutions and suspensions includes, for example, distilled water and physiological saline for injections. The diluent for the non-aqueous solutions and suspensions includes, for example, propylene glycol, polyethylene glycol, vegetable oils such as olive oil, alcohols such as ethyl alcohol, Polysolvate 80 (trade name).

Those compositions may further contain additives such as isotonicity regulators, preservatives, wetting promoters, emulsifiers, dispersants, stabilizers (e.g., lactose), solubilizers, dissolution promoters. These are sterilized by filtering them through bacteria-trapping filters, or by adding microbicides thereto, or by exposing them to radiations. Germ-free, solid compositions may be produced previously, and they may be dissolved in germ-free water or in germ-free solvents for injection, before using them.

BEST MODES OF CARRYING OUT THE INVENTION

The invention is described concretely with reference to the following Examples, which, however, are not intended to restrict the scope of the invention. Some starting compounds used in the Examples are novel, and methods of producing them from known compounds are described as Reference Examples.

REFERENCE EXAMPLE 1

A suspension of 1.4 g of (2S,4S)-4-fluoropyrrolidine-2-carboxamide monohydrochloride prepared according to the similar method as that described in a patent reference (International Publication WO02/38451 pamphlet), and 3.0 ml of N,N-diisopropylethylamine in 10 ml of chloroform was added dropwise to a solution of 0.73 ml of chloroacetyl chloride in 14 ml of chloroform under cooling with an ice-water bath, and the reaction mixture was stirred for 30 minutes under cooling with an ice-water bath. Then, the reaction mixture was concentrated under reduced pressure. To a solution of the resulting residue in 14 ml of chloroform, 2.4 ml of trifluoroacetic anhydride was added dropwise under cooling with an ice-water bath. Then, the reaction mixture was allowed to room temperature, and stirred for 1 hour. This was concentrated under reduced pressure, and 0.1 M hydrochloric acid was added to the resulting residue, and this was then extracted with ethyl acetate. The organic layer was dried over anhydrous magnesium sulfate. The drying agent was removed, and the solvent was removed under reduced pressure. The resulting residue was purified with silica gel column chromatography (eluent: chloroform to chloroform/methanol=30/1) to obtain 0.84 g of (2S,4S)-1-(chloroacetyl)-4-fluoropyrrolidine-2-carbonitrile.

NMR: 2.33-2.67 (2H,m), 3.60-4.05 (2H,m), 4.35-4.55 (2H,m), 4.95-5.05, 5.30-5.60 (2H,m).

In the same manner as in Reference Example 1, the compounds of Reference Examples 2 to 4 shown in Table 4 were prepared from the corresponding starting compounds.

REFERENCE EXAMPLE 5

To a suspension of 790 mg of tert-butyl exo-8-azabicyclo[3.2.1]oct-3-ylcarbamate hydrochloride prepared according to the method described in *J. Med. Chem.* (1991), 34, 656-663 or *J. Heterocycl. Chem.* (1892), 19, 485-488, in 10 ml of methylene chloride and 5 ml of N,N-dimethylformamide, were added 1.3 g of triethylamine and 1.05 g of methanesulfonyl chloride. The reaction mixture was stirred at room temperature for 1 day and concentrated under reduced pressure. Water was added to the resulting residue, and this was extracted with ethyl acetate. The organic layer was washed with brine, and then dried over anhydrous magnesium sulfate, and the solvent was removed under reduced pressure. The resulting residue was purified with silica gel column chromatography (eluent: hexane/ethyl acetate=7/3) and crystallized from diethyl ether-hexane to obtain 600 mg of tert-butyl exo-8-(methanesulfonyl)-8-azabicyclo[3.2.1]oct-3-ylcarbamate as a colorless solid.

In the same manner as in Reference Example 5, the compounds of Reference Examples 6 to 16 shown in Table 4 were prepared from the corresponding starting compounds.

REFERENCE EXAMPLE 17

A chloroform solution of 2.0 g of tert-butyl piperidin-4-ylcarbamate was added to a mixed solution of 4.7 ml of acetic anhydride and 1.9 ml of formic acid, and the reaction mixture was stirred at room temperature for 15 hours. Water was added to the reaction mixture, and this was extracted with EtOAc. The organic layer was washed with 1 M hydrochloric acid, aqueous saturated sodium hydrogencarbonate and brine. This was dried with anhydrous magnesium sulfate, and the solvent was removed under reduced pressure. The resulting residue was purified with silica gel column chromatography (eluent: chloroform/MeOH=50/1) to obtain 1.7 g of tert-butyl (1-formylpiperidin-4-yl)carbamate.

In the same manner as in Reference Example 17, the compound of Reference Example 18 shown in Table 4 was prepared from the corresponding starting compound.

REFERENCE EXAMPLE 19

To a solution of 3.0 g of tert-butyl piperidin-4-ylcarbamate in 60 ml of methylene chloride, were added 2.5 ml of triethylamine, 2.4 g of HOBt, 1.3 g of hydroxyacetic acid and 3.5 g of WSCD hydrochloride, and the reaction mixture was stirred at room temperature for 18 hours. 1 M hydrochloric acid was added to the reaction mixture, and this was extracted with EtOAc. The organic layer was washed with aqueous saturated sodium hydrogencarbonate solution, water and brine. This was dried over anhydrous magnesium sulfate, and the solvent was removed under reduced pressure. The resulting residue was purified with silica gel column chromatography (eluent: chloroform/MeOH=50/1) to obtain 2.8 g of tert-butyl [1-(hydroxyacetyl)piperidin-4-yl]carbamate.

In the same manner as in Reference Example 19, the compounds of Reference Examples 20 to 24 shown in Table 4 were produced from the corresponding starting compounds.

REFERENCE EXAMPLE 25

A suspension of 1.0 g of tert-butyl piperidin-4-ylcarbamate hydrochloride and 0.6 ml of triethylamine in 15 ml of methylene chloride was added to a solution of 418 mg of triphosgene in 10 ml of methylene chloride under cooling with ice-water bath. The reaction mixture was stirred for 2 hours with ice cooling, and then a solution of 358 mg of piperidine and 0.6 ml of triethylamine in 5 ml of methylene chloride was added thereto and stirred at room temperature for 15 hours. Aqueous 10% citric acid solution was added to the reaction mixture, and this was extracted with EtOAc. The organic layer was washed with brine, and then dried over anhydrous magnesium sulfate, and the solvent was removed under reduced pressure. The resulting solid was washed with ether to obtain 440 mg of tert-butyl [1-(piperidine-1-carbonyl)piperidin-4-yl]carbamate.

In the same manner as in Reference Example 25, the compounds of Reference Examples 26 and 27 shown in Table 4 were produced from the corresponding starting compounds.

REFERENCE EXAMPLE 28

2.0 g of m-chloroperbenzoic acid was added to 1.0 g of tert-butyl [1-(thiomorpholine-4-carbonyl)piperidin-4-yl]carbamate in 10 ml of methylene chloride under cooling with ice-water bath. The reaction mixture was allowed to room temperature, and stirred for 18 hours. Aqueous saturated sodium thiosulfate solution was added to the reaction mixture, and this was extracted with EtOAc. The organic layer was washed with aqueous saturated sodium hydrogencarbonate and brine, and dried over anhydrous magnesium sulfate, and the solvent was removed under reduced pressure. The resulting solid was washed with diisopropyl ether to obtain 607 mg of tert-butyl [1-(1,1-dioxothiomorpholine-4-carbonyl)piperidin-4-yl]carbamate.

REFERENCE EXAMPLE 29

A solution of 500 mg of tert-butyl piperidin-4-ylcarbamate and 345 mg of ethyl fluoroacetate in 1 ml of trifluoroethanol was heated under reflux for 8 hours. The reaction mixture was concentrated under reduced pressure, and 1 M hydrochloric acid was added to the resulting residue. Then, this was extracted with EtOAc, and the organic layer was washed with aqueous saturated sodium hydrogencarbonate and brine. This was then dried over anhydrous magnesium sulfate, and the solvent was removed under reduced pressure. The resulting residue was purified with silica gel column chromatography (eluent: chloroform to chloroform/methanol=30/1) to obtain 345 mg of tert-butyl [1-(fluoroacetyl)piperidin-4-yl]carbamate.

In the same manner as in Reference Example 29, the compound of Reference Example 30 shown in Table 4 was produced from the corresponding starting compound.

REFERENCE EXAMPLE 31

15 ml of 4 M hydrogen chloride in EtOAc was added to a solution of 500 mg of the compound of Reference Example 5 in 15 ml of EtOAc, and the reaction mixture was stirred at room temperature for 9 hours. The resulting solid was collected by filtration to obtain 400 mg of a colorless solid of exo-8-(methanesulfonyl)-8-azabicyclo[3.2.1]oct-3-ylamine hydrochloride.

In the same manner as in Reference Example 31, the compounds of Reference Examples 32 to 49 shown in Table 4 were produced from the corresponding starting compounds.

REFERENCE EXAMPLE 50

300 mg of 10% palladium on carbon was added to a solution of 1.4 g of the compound of Reference Example 22 in 30 ml of MeOH, and the reaction mixture was stirred overnight under atmospheric hydrogen at room temperature. The insoluble matter was removed by filtration, and the filtrate was concentrated under reduced pressure to obtain 400 mg of a colorless solid of 2-(4-amino-4-methylpiperidin-1-yl)-2-oxoethanol.

In the same manner as in Reference Example 50, the compounds of Reference Examples 51 to 55 shown in Table 4 were produced from the corresponding starting compounds.

REFERENCE EXAMPLE 56

20 ml of 6 M hydrochloric acid was added to 2.2 g of the compound of Reference Example 42, and the reaction mixture was refluxed for 24 hours. The reaction mixture was concentrated, and toluene and MeOH were added to the residue, and this was concentrated again. The resulting residue was crystallized from MeOH-diethyl ether, and collected to obtain 1.22 g of [4-amino-1-(methanesulfonyl)piperidin-4-yl]methanol.

The meanings of the abbreviations in the Table are mentioned below (the same shall apply hereinunder).

Rf: Number of Reference Example

Salt: salt (HCl: hydrochloride, fum: fumarate, not described: free compound)

Structure: Structural formula

Data: Physicochemical data (NMR: peak δ [ppm] in $^1$H-NMR, in which the internal standard is $(CH_3)_4Si$ and the solvent for measurement is DMSO-$d_6$, FAB-MS: FAB mass spectral data, m.p.: melting point)

Me: methyl, Boc: t-butyloxycarbonyl, Ms: methanesulfonyl, Bn: benzyl

TABLE 4

| Rf (Salt) | Structure (Data) |
|---|---|
| 1 | 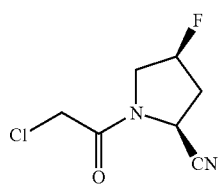 (FAB-MS:191.) |
| 2 | 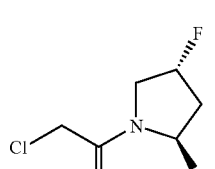 (FAB-MS:191.) |

TABLE 4-continued

| Rf (Salt) | Structure (Data) |
|---|---|
| 3 | 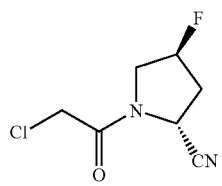 (FAB-MS:191.) |
| 4 | 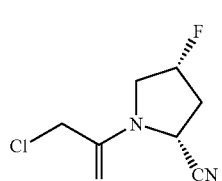 (FAB-MS:191.) |
| 5 | 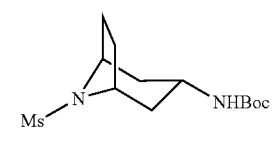 (FAB-MS:305.) |
| 6 | 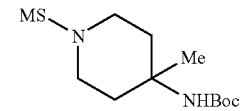 (FAB-MS:293.) |
| 7 | 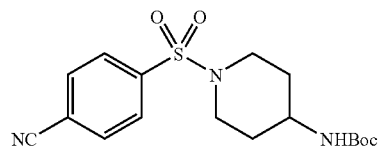 (FAB-MS:366.) |
| 8 | 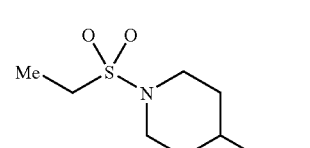 (FAB-MS:293.) |
| 9 | 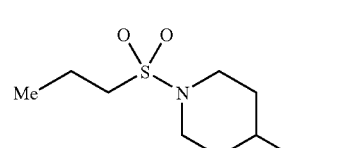 (FAB-MS:307.) |

TABLE 4-continued

| Rf (Salt) | Structure (Data) |
|---|---|
| 10 | Me-CH(Me)-S(O)₂-N(piperidine)-NHBoc (FAB-MS:307.) |
| 11 | Me-S(O)₂-N(pyrrolidine)-NHBoc (FAB-MS:265.) |
| 12 | Me-S(O)₂-N(pyrrolidine)-NHBoc (FAB-MS:265.) |
| 13 | Me-S(O)₂-N(piperidine)(CH₂OBn)(NHBoc) (FAB-MS:399.) |
| 14 | Me-CH₂CH₂-S(O)₂-N(piperidine)(Me)(NHCO₂Bn) (FAB-MS:355.) |
| 15 | Me-CH₂-S(O)₂-N(piperidine)(Me)(NHCO₂Bn) (FAB-MS:341.) |
| 16 | Ms-N(piperidine)(Me)(NHCO₂Bn) (FAB-MS:327.) |
| 17 | H-C(O)-N(piperidine)-NHBoc (FAB-MS:229.) |
| 18 | H-C(O)-N(piperidine)(Me)(NHCO₂Bn) (FAB-MS:277.) |
| 19 | HO-CH₂-C(O)-N(piperidine)-NHBoc (FAB-MS:259.) |
| 20 | HO-C(Me)₂-C(O)-N(piperidine)-NHBoc (FAB-MS:287.) |
| 21 | dimethyl-dioxolane-C(O)-N(piperidine)-NHBoc (FAB-MS:329.) |
| 22 | HO-CH₂-C(O)-N(piperidine)(Me)(NHCO₂Bn) (FAB-MS:307.) |
| 23 | dimethyl-dioxolane-C(O)-N(piperidine)-NHBoc (FAB-MS:329.) |
| 24 | HO-(CH₂)₃-C(O)-N(piperidine)-NHBoc (FAB-MS:287.) |

TABLE 4-continued

| Rf (Salt) | Structure (Data) |
|---|---|
| 25 | (FAB-MS:312.) |
| 26 | (FAB-MS:328.) |
| 27 | (FAB-MS:330.) |
| 28 | (FAB-MS:362.) |
| 29 | (FAB-MS:261.) |
| 30 | (FAB-MS:309.) |
| 31 (HCl) | (FAB-MS:205.) |
| 32 (HCl) | (FAB-MS:193.) |
| 33 (HCl) | (FAB-MS:266.) |
| 34 (HCl) | (FAB-MS:193.) |
| 35 (HCl) | (FAB-MS:207.) |
| 36 (HCl) | (FAB-MS:207.) |
| 37 (HCl) | (FAB-MS:129.) |
| 38 (HCl) | (FAB-MS:159.) |

TABLE 4-continued

| Rf (Salt) | Structure (Data) |
|---|---|
| 39 (HCl) | 2-hydroxy-2-methylpropanoyl-4-aminopiperidine (FAB-MS:187.) |
| 40 (HCl) | (3R)-1-(methylsulfonyl)pyrrolidin-3-amine (FAB-MS:165.) |
| 41 (HCl) | (3S)-1-(methylsulfonyl)pyrrolidin-3-amine (FAB-MS:165.) |
| 42 (HCl) | 4-(benzyloxymethyl)-1-(methylsulfonyl)piperidin-4-amine (FAB-MS:299.) |
| 43 (HCl) | [1,4'-bipiperidine]-1'-carbonyl, 4-amino (FAB-MS:212.) |
| 44 (HCl) | 4-hydroxy-[1,4'-bipiperidine]-1'-carbonyl, 4'-amino (FAB-MS:228.) |
| 45 (HCl) | (2R)-2,3-dihydroxy-1-(4-aminopiperidin-1-yl)propan-1-one (FAB-MS:189.) |
| 46 (HCl) | (2S)-2,3-dihydroxy-1-(4-aminopiperidin-1-yl)propan-1-one (FAB-MS:189.) |
| 47 (HCl) | thiomorpholine-1,1-dioxide-4-carbonyl-4-aminopiperidine (FAB-MS:262.) |
| 48 (HCl) | 4-hydroxy-1-(4-aminopiperidin-1-yl)butan-1-one (FAB-MS:187.) |
| 49 (HCl) | 2-fluoro-1-(4-aminopiperidin-1-yl)ethan-1-one (FAB-MS:161.) |
| 50 | 2-hydroxy-1-(4-amino-4-methylpiperidin-1-yl)ethan-1-one (FAB-MS:173.) |
| 51 | 4-methyl-1-(methylsulfonyl)piperidin-4-amine (FAB-MS:193.) |
| 52 | 1-(ethylsulfonyl)-4-methylpiperidin-4-amine (FAB-MS:207.) |
| 53 | 4-methyl-1-(propylsulfonyl)piperidin-4-amine (FAB-MS:221.) |

TABLE 4-continued

| Rf (Salt) | Structure (Data) |
|---|---|
| 54 | 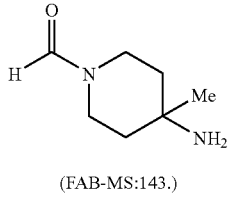<br>(FAB-MS:143.) |
| 55 | 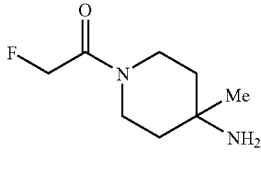<br>(EI-MS:174.) |
| 56 (HCl) | 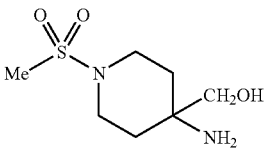<br>(FAB-MS:209.) |

EXAMPLE 1

To a suspension of 451 mg of 1-(methanesulfonyl)piperidine-4-amine monohydrochloride prepared according to the method described in International Publication WO0218380 pamphlet, and 435 mg of potassium carbonate in 8 ml of acetonitrile, was added 200 mg of (2S,4S)-1-(chloroacetyl)-4-fluoropyrrolidine-2-carbonitrile, and the reaction mixture was stirred at room temperature for 4 days. The insoluble material was removed by filtration, and 1.20 g of silica gel was added to the filtrate, and the reaction mixture was concentrated under reduced pressure. The resulting residue was purified with silica gel column chromatography (eluent: chloroform/methanol/aqueous 28% ammonia=100/1/0.1 to 20/1/0.1) to obtain 487 mg of a colorless amorphous. 10 ml of ethanol was added to the resulting colorless amorphous, and the reaction mixture stirred at room temperature for 30 minutes. The insoluble material was collected by filtration, washed with ethanol, and dried under reduced pressure. 230 mg of the resulting colorless solid was dissolved in 2 ml of tetrahydrofuran and 4 ml of methanol, to which was added 80 mg of fumaric acid. The resulting solution was concentrated under reduced pressure until the amount of the solvent became about 2 ml, and then 5 ml of ethanol was added to it and the mixture was stirred at room temperature for 30 minutes. The precipitation was collected by filtration, washed with ethanol and dried under reduced pressure to obtain 217 mg of a colorless crystal of (2S,4S)-4-fluoro-1-({[1-(methanesulfonyl)piperidin-4-yl]amino}acetyl)pyrrolidine-2-carbonitrile monofumarate.

In the same manner as in Example 1, the compounds of Examples 2 to 47 Table 5 and Table 6 were prepared from the corresponding starting compounds.

The meanings of the abbreviations in the Tables are mentioned below (the same shall apply hereinunder).

Ex: Number of Example
A: Substituent in general formula
tBu: t-butyl, Et: ethyl, n-Pr: n-propyl, i-Pr: isopropyl, Ac: acetyl

TABLE 5

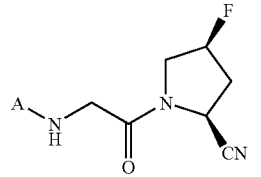

| Ex Salt | A (Data) |
|---|---|
| 1 (fum) | 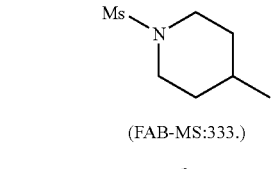<br>(FAB-MS:333.) |
| 2 (fum) | 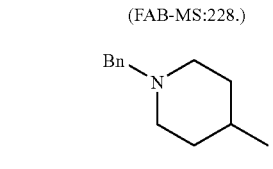<br>(FAB-MS:228.) |
| 3 (fum) | 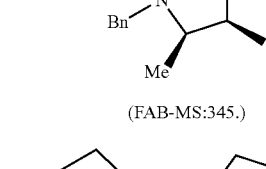<br>(FAB-MS:345.) |
| 4 (fum) | 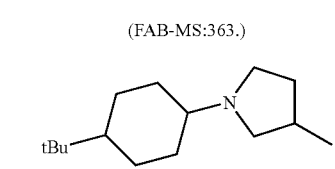<br>(FAB-MS:345.) |
| 5 (fum) | 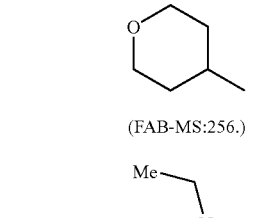<br>(FAB-MS:363.) |
| 6 (fum) | <br>(FAB-MS:379.) |
| 7 (fum) | <br>(FAB-MS:256.) |
| 8 (fum) |  |

TABLE 5-continued
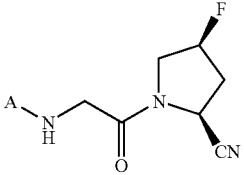
| Ex Salt | A (Data) |
|---|---|
| | (FAB-MS:298.) |
| 9 (fum) | 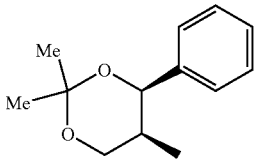 (FAB-MS:362.) |
| 10 (fum) |  (FAB-MS:356.) |
| 11 (fum) | 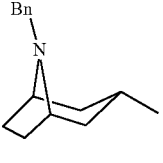 (FAB-MS:357.) |
| 12 (fum) | 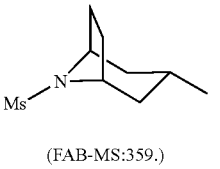 (FAB-MS:371.) |
| 13 (fum) | 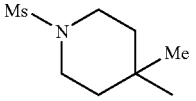 (FAB-MS:359.) |
| 14 (fum) | 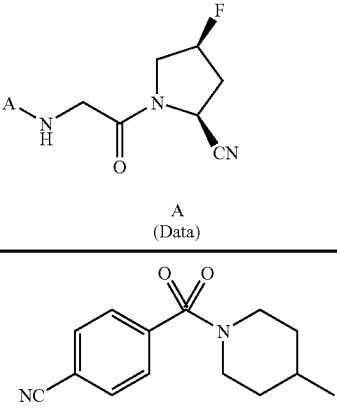 (FAB-MS:347.) |
TABLE 5-continued
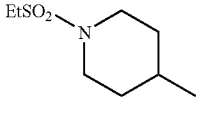
| Ex Salt | A (Data) |
|---|---|
| 15 (fum) | 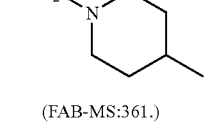 (FAB-MS:420.) |
| 16 (fum) | 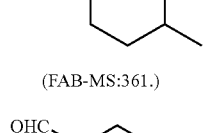 (FAB-MS:333.) |
| 17 (fum) | 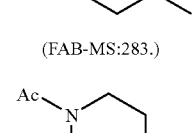 (FAB-MS:361.) |
| 18 (fum) | 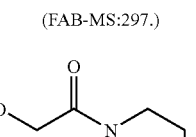 (FAB-MS:361.) |
| 19 (fum) | 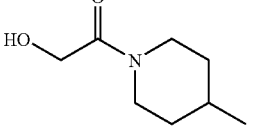 (FAB-MS:283.) |
| 20 (fum) | 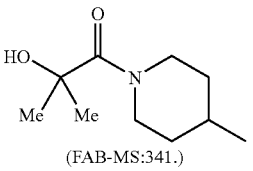 (FAB-MS:297.) |
| 21 (fum) |  (FAB-MS:3 13.) |
| 22 (fum) |  (FAB-MS:341.) |

TABLE 5-continued
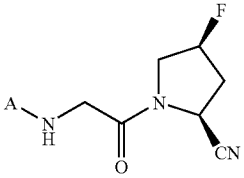
| Ex Salt | A (Data) |
|---|---|
| 23 (fum) | 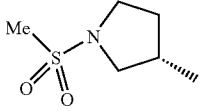<br>(FAB-MS:326.) |
| 24 (fum) | 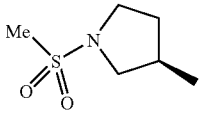<br>(FAB-MS:319.) |
| 25 (fum) | 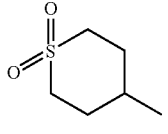<br>(FAB-MS:319.) |
| 26 (fum) | 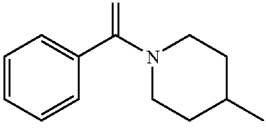<br>(FAB-MS:304.) |
| 27 (fum) | 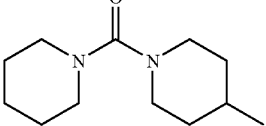<br>(FAB-MS:359.) |
| 28 (fum) | 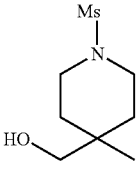<br>(FAB-MS:368.) |
| 29 (fum) | 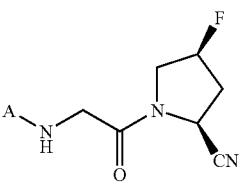<br>(FAB-MS:363.) |
TABLE 5-continued
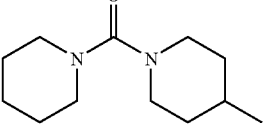
| Ex Salt | A (Data) |
|---|---|
| 30 (fum) | 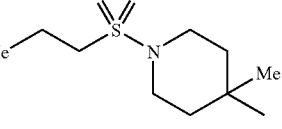<br>(FAB-MS:366.) |
| 31 (fum) | 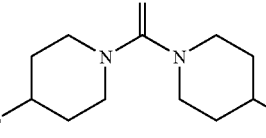<br>(FAB-MS:375.) |
| 32 (fum) | 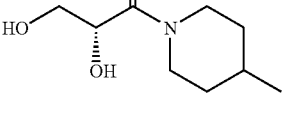<br>(FAB-MS:382.) |
| 33 (fum) | 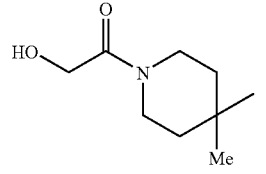<br>(FAB-MS:343.) |
| 34 (fum) | 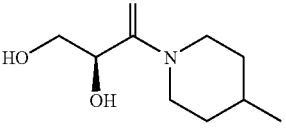<br>(FAB-MS:327.) |
| 35 (fum) | <br>(FAB-MS:343.) |

TABLE 5-continued

| Ex Salt | A (Data) |
|---|---|
| 36 (fum) | 4,4-dimethylpiperidine-1-carbaldehyde (FAB-MS: 297.) |
| 37 (fum) | 1-(ethylsulfonyl)-4,4-dimethylpiperidine (FAB-MS: 361.) |
| 38 (fum) | (1,1-dioxidothiomorpholin-4-yl)(4-methylpiperidin-1-yl)methanone (FAB-MS: 416.) |
| 39 (fum) | 4-hydroxy-1-(4-methylpiperidin-1-yl)butan-1-one (FAB-MS: 341.) |
| 40 (fum) | 2-fluoro-1-(4-methylpiperidin-1-yl)ethanone (FAB-MS: 315.) |
| 41 (fum) | 2-fluoro-1-(4,4-dimethylpiperidin-1-yl)ethanone (FAB-MS: 329.) |

TABLE 6

| Ex Salt | Structure (Data) |
|---|---|
| 42 (fum) | (FAB-MS: 347.) |
| 43 (fum) | (FAB-MS: 347.) |
| 44 (fum) | (FAB-MS: 347.) |
| 45 (fum) | (FAB-MS: 327.) |
| 46 (fum) | (FAB-MS: 327.) |
| 47 (fum) | (FAB-MS: 327.) |

Hereinafter, the NMR data of some example compounds are shown in Table 7.

TABLE 7

| Ex (Salt) | Data |
|---|---|
| 1 (fum) | NMR: 1.30-1.50(2H, m), 1.65-2.05(2H, m), 2.20-2.60(2H, m), 2.60-3.00(6H, m), 3.40-3.85(5H, m), 3.85-4.02(1H, m), 4.90-5.04, 5.30-5.60(2H, m), 6.57(2H, s). |
| 2 (fum) | NMR: 1.95-2.40(2H, m), 3.30-4.30(9H, m), 4.40-4.75, 5.20-5.60(2H, m), 6.55(2H, s). |
| 3 (fum) | NMR: 1.30-1.50(2H, m), 1.75-1.90(2H, m), 1.95-2.15(2H, m), 2.25-2.70(3H, m), 2.75-2.95(2H, m), 3.45-3.60(3H, m), 3.60-3.85(2H, m), 3.85-4.20(1H, m), 4.80-5.38, 5.38-5.60(2H, m), 6.56(2H, s), 7.20-7.37(5H, m). |
| 4 (fum) | NMR: 1.00-1.15(3H, m), 1.45-1.70(1H, m), 1.90-2.10(1H, m), 2.25-2.75(3H, m), 2.75-2.95(2H, m), 3.12-3.25(1H, m), 3.25-4.10(6H, m), 4.90-5.38, 5.38-5.60(2H, m), 6.58(2H, s), 7.20-7.40(5H, m). |
| 5 (fum) | NMR: 1.25-2.05(16H, m), 2.20-2.90(5H, m), 3.00-4.00(7H, m), 4.75-5.38, 5.38-5.60(2H, m), 6.54(2H, s). |
| 6 (fum) | NMR: 0.75-0.90(9H, m), 0.90-1.10(2H, m), 1.20-1.55(7H, m), 1.55-2.10(4H, m), 2.10-4.05(10H, m), 4.60-5.38, 5.38-5.60(2H, m), 6.55(4H, s). |
| 7 (fum) | NMR: 1.20-1.45(2H, m), 1.70-1.90(2H, m), 2.30-2.60(2H, m), 2.60-2.90(1H, m), 3.20-3.35(2H, m), 3.35-3.55(1H, m), 3.55-3.70(2H, m), 3.70-4.05(3H, m), 4.90-5.34, 5.34-5.60(2H, m), 6.57(2H, s). |
| 8 (fum) | NMR: 0.98(6H, t), 2.25-2.80(8H, m), 3.00-3.20(2H, m), 3.30-3.80(5H, m), 3.80-4.30(1H, m), 4.70-5.38(1H, m), 5.38-5.65(1H, m), 3.70-4.05(3H, m), 4.90-5.34, 5.34-5.60(2H, m), 6.60(4H, s). |
| 9 (fum) | NMR: 1.35-1.55(6H, m), 2.10-2.45(2H, m), 2.60-2.75(1H, m), 2.98-3.65(4H, m), 3.80-3.95(1H, m), 4.00-4.35(1H, m), 4.70-4.95, 5.15-5.40(3H, m), 6.59(2H, s), 7.15-7.45(5H, m). |
| 10 (fum) | NMR: 1.24-1.50(2H, m), 1.70-2.04(2H, m), 2.30-3.04(4H, m), 3.40-4.15(7H, m), 4.90-5.05, 5.30-5.60(2H, m), 6.58(2H, s), 7.02(2H, d), 7.55(2H, d). |
| 11 (fum) | NMR: 1.20-1.40(2H, m), 1.70-2.00(2H, m), 2.30-3.20(4H, m), 3.40-4.10(5H, m), 4.20-4.40(2H, m), 4.90-5.60(2H, m), 6.57(2H, s), 6.95(1H, d), 7.83(1H, m), 8.45(1H, d). |
| 13 (fum) | NMR: 1.35-1.53(2H, m), 1.55-1.75(2H, m), 1.85-2.05(4H, m), 2.30-2.60(2H, m), 2.88-3.04(4H, m), 3.35-4.00(4H, m), 4.05-4.25(2H, m), 4.90-5.04, 5.28-5.60(2H, m). |
| 14 (fum) | NMR: 1.05-1.20(3H, s), 1.45-1.80(4H, m), 2.30-2.65(2H, m), 2.85(3H, s), 3.00-3.30(4H, m), 3.35-3.85(3H, m), 3.92-4.10(1H, m), 4.97-5.02, 5.30-5.62(2H, m), 6.58(2H, s). |
| 15 (fum) | NMR: 1.25-1.60(2H, m), 1.60-2.05(2H, m), 2.20-2.90(5H, m), 3.00-4.25(6H, m), 4.70-5.00, 5.20-5.60(2H, m), 6.52(1H, s), 7.70-8.00(2H, m), 8.05-8.20(2H, m). |
| 19 (fum) | NMR: 1.04-1.35(2H, m), 1.75-1.95(2H, m), 2.30-2.60(2H, m), 2.65-2.90(2H, m), 3.01-3.10(1H, m), 3.38-4.05(6H, m), 4.96-5.35, 5.36-5.56(2H, m), 6.58(2H, s), 7.97(1H, s). |
| 21 (fum) | NMR: 1.05-1.40(2H, m), 1.86(2H, br), 2.30-2.65(1H, m), 2.77-2.81(2H, m), 2.90-3.05(1H, m), 3.47-4.16(11H, m), 4.98-5.40, 5.34-5.57(2H, m), 6.58(2H, s). |
| 28 (fum) | NMR: 1.20-1.36(2H, m), 1.72-1.90(2H, m), 2.30-2.62(1H, m), 2.70-2.82(3H, m), 3.05-3.15(4H, m), 3.50-4.00(9H, m), 4.95-5.37(1H, m), 5.40-5.60(1H, m), 6.57(2H, s). |
| 34 (fum) | NMR: 1.05-1.20(3H, s), 1.30-1.70(4H, m), 2.30-2.65(2H, m), 3.10-4.10(10H, m), 4.92-5.05, 5.32-5.62(2H, m), 6.58(2H, s). |
| 36 (fum) | NMR: 1.08, 1.11(3H, s), 1.30-1.65(4H, m), 2.30-2.70(2H, m), 3.20-4.10(8H, m), 4.90-5.05, 5.33-5.60(2H, m), 6.59(2H, s), 7.96(1H, s). |
| 41 (fum) | NMR: 1.06, 1.08(3H, s), 1.38-1.56(4H, m), 2.33-2.67(2H, m), 3.17-4.03(8H, m), 4.98-5.57(4H, m), 6.60(2H, s). |

Structures of other compounds of the invention will be shown in Table 8. These can be readily prepared according to the production methods mentioned above, according to the methods described in Examples, according to any other methods obvious to those skilled in the art, or according to modifications of those methods.

The meaning of the abbreviation in the Table is mentioned below.
No: Number of Compound
TABLE 8
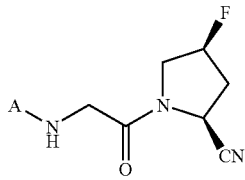
| No | A | No | A |
|---|---|---|---|
| P1 | 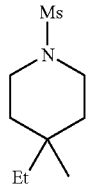 | P2 | 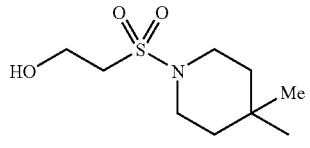 |
| P3 | 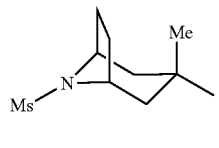 | P4 | 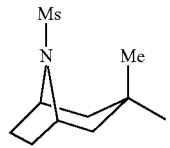 |
| P5 | 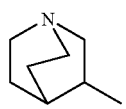 | P6 | 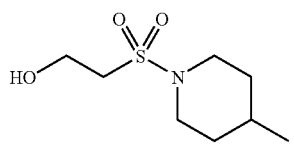 |
| P7 | 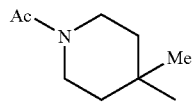 | P8 | 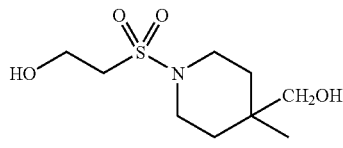 |
| P9 | 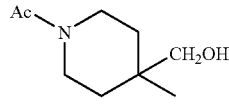 | P10 | 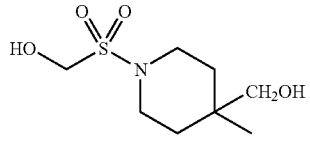 |
| P11 | 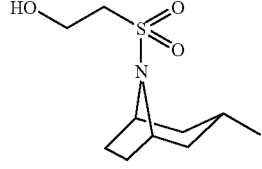 | P12 | 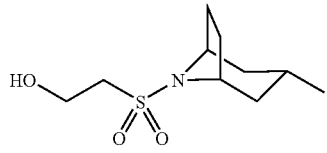 |
| P13 | 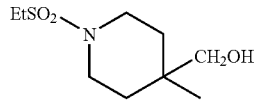 | P14 | 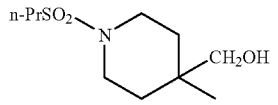 |
| P15 | 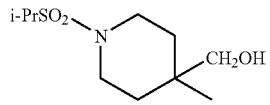 | P16 | 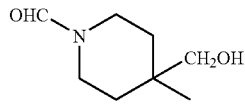 |

TABLE 8-continued
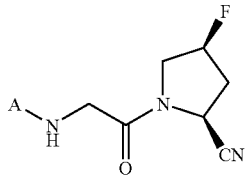
| No | A | No | A |
|---|---|---|---|
| P17 | 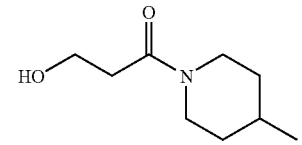 | P18 | 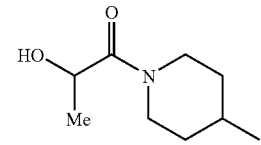 |
| P19 | 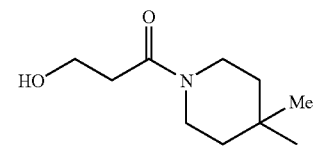 | P20 | 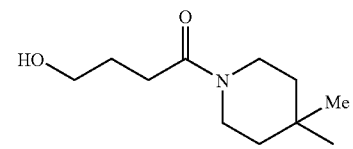 |
| P21 | 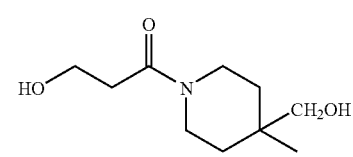 | P22 | 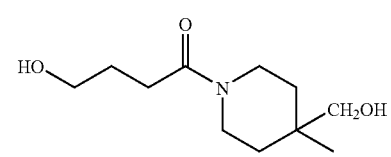 |
| P23 | 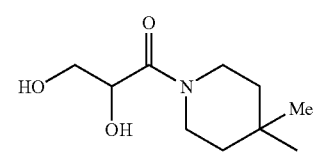 | P24 | 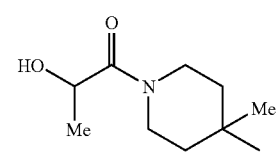 |
| P25 | 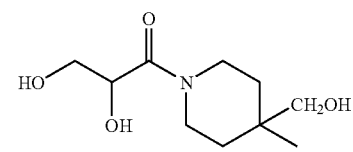 | P26 | 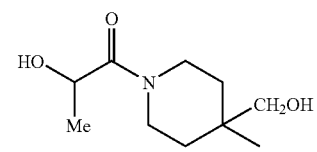 |
| P27 | 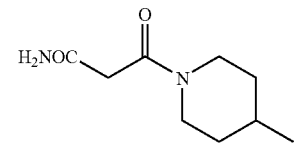 | P28 | 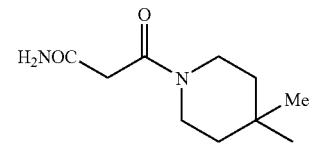 |
| P29 | 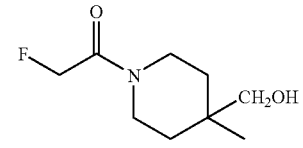 | P30 | 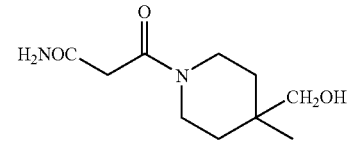 |
| P31 | 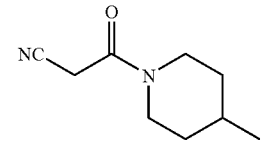 | P32 | 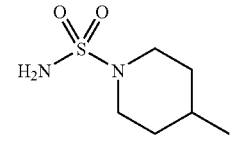 |

TABLE 8-continued

| No | A | No | A |
|---|---|---|---|
| P33 | NC-C(=O)-N-piperidine-4,4-diMe (with Me shown) | P34 | H2N-S(=O)2-N-piperidine-4-Me |
| P35 | NC-C(=O)-N-piperidine-4-Me-4-CH2OH | P36 | H2N-S(=O)2-N-piperidine-4-Me-4-CH2OH |

The invention claimed is:

1. A 2-cyano-4-fluoropyrrolidine compound of Formula (I):

(I)

wherein A is a group of Formula (II):

(II)

wherein $R^1$-B represents methanesulfonyl, formyl or acetyl which may be substituted by a group selected from the group consisting of —OH and fluoro;

$R^2$ represents —H, methyl or ethyl;

or a pharmaceutically acceptable salt thereof.

2. A compound selected from the group consisting of:
4-fluoro-1-({[1-(methanesulfonyl)piperidin-4-yl]amino}acetyl)pyrrolidine-2-carbonitrile,
4-fluoro-1-({[4-methyl-1-(methanesulfonyl)piperidin-4-yl]amino}acetyl)pyrrolidine-2-carbonitrile,
4-fluoro-1-{[(1-glycoloylpiperidin-4-yl)amino]acetyl}pyrrolidine-2-carbonitrile,
4-fluoro-1-{[(1-glycoloyl-4-methylpiperidin-4-yl)amino]acetyl}pyrrolidine-2-carbonitrile
4-fluoro-1-{[(1-fluoroacetyl-4-methylpiperidin-4-yl)amino]acetyl}pyrrolidine -2-carbonitrile,
4-fluoro-1-{[(1-formylpiperidin-4-yl)amino]acetyl}pyrrolidine-2-carbonitrile,
4-fluoro-1-{[(1-formyl-4-methylpiperidin-4-yl)amino]acetyl}pyrrolidine-2-carbonitrile, and
4-fluoro-1-({[1-(morpholin-4-ylcarbonyl)piperidin-4-yl]amino}acetyl)pyrrolidine-2-carbonitrile,
or a pharmaceutically acceptable salt thereof.

3. A pharmaceutical composition comprising an effective amount of the compound or pharmaceutical acceptable salt thereof of claim 1 as an active ingredient, and a pharmaceutically acceptable carrier.

4. The compound according to claim 1, wherein the compound is selected from the group consisting of:
(2S,4S)-4-fluoro-1-({[4-methyl-1-(methanesulfonyl)piperidin-4-yl]amino}acetyl)pyrrolidine-2-carbonitrile,
(2S,4S)-4-fluoro-1-{[(1-glycoloyl-4-methylpiperidin-4-yl)amino]acetyl}pyrrolidine-2-carbonitrile,
(2S,4S)-4-fluoro-1-{[(1-fluoroacetyl-4-methylpiperidin-4-yl)amino]acetyl}pyrrolidine-2-carbonitrile, and
(2S,4S)-4-fluoro-1-{[(1-formyl-4-methylpiperidin-4-yl)amino]acetyl}pyrrolidine-2-carbonitrile,
or a pharmaceutically acceptable salt thereof.

5. A pharmaceutical composition comprising an effective amount of the compound or pharmaceutical acceptable salt thereof of claim 4 as an active ingredient, and a pharmaceutically acceptable carrier.

* * * * *

UNITED STATES PATENT AND TRADEMARK OFFICE
CERTIFICATE OF CORRECTION

| | |
|---|---|
| PATENT NO. | : 7,268,150 B2 |
| APPLICATION NO. | : 10/492347 |
| DATED | : September 11, 2007 |
| INVENTOR(S) | : Hayakawa et al. |

It is certified that error appears in the above-identified patent and that said Letters Patent is hereby corrected as shown below:

Claim 2, column 38, line 32, after "acetyl}pyrrolidine-2-carbonitrile" insert a comma.

Signed and Sealed this

Fourth Day of March, 2008

JON W. DUDAS
*Director of the United States Patent and Trademark Office*